(12) United States Patent
Gannot et al.

(10) Patent No.: US 8,547,236 B2
(45) Date of Patent: *Oct. 1, 2013

(54) SYSTEM FOR AUTOMATIC FALL DETECTION FOR ELDERLY PEOPLE

(75) Inventors: Israel Gannot, Ramat-HaSharon (IL); Dimitry Litvak, Tel-Aviv (IL); Yaniv Zigel, Omer (IL)

(73) Assignees: Ramot at Tel-Aviv University Ltd., Tel-Aviv (IL); Ben-Gurion University of the Negev Research and Development Authority, Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/453,012

(22) Filed: Apr. 23, 2012

(65) Prior Publication Data

US 2012/0206264 A1 Aug. 16, 2012

Related U.S. Application Data

(63) Continuation of application No. 12/320,521, filed on Jan. 28, 2009, now Pat. No. 8,179,268.

(60) Provisional application No. 61/064,508, filed on Mar. 10, 2008.

(51) Int. Cl.
*G08B 23/00* (2006.01)
(52) U.S. Cl.
USPC ............... 340/573.1; 340/540; 340/573.4
(58) Field of Classification Search
USPC ................................... 340/573.1
See application file for complete search history.

(56) References Cited

U.S. PATENT DOCUMENTS

| 5,924,105 | A | 7/1999 | Punch, III et al. |
| 6,433,690 | B2 | 8/2002 | Petelenz et al. |
| 7,302,826 | B2 * | 12/2007 | Yoon ........................... 73/12.01 |
| 7,961,109 | B2 | 6/2011 | Jang et al. |
| 2002/0044682 | A1 | 4/2002 | Weil et al. |
| 2009/0224925 | A1 | 9/2009 | Gannot et al. |

FOREIGN PATENT DOCUMENTS

WO WO 2009113056 9/2009

OTHER PUBLICATIONS

International Preliminary Report on Patentability Dated Sep. 23, 2010 From the International Bureau of WIPO Re. Application No. PCT/IL2009/000262.
International Search Report and the Written Opinion Dated Jun. 22, 2010 From the International Searching Authority Re. Application No. PCT/IL2009/000262.
Official Action Dated Jul. 11, 2011 From the US Patent and Trademark Office Re. U.S. Appl. No. 12/320,521.
Official Action Dated Oct. 21, 2011 From the US Patent and Trademark Office Re. U.S. Appl. No. 12/320,521.

(Continued)

*Primary Examiner* — Kerri McNally

(57) ABSTRACT

Apparatus for detection of human falls comprises: an acceleration detector, for detecting vibration events, typically placed on a floor, a microphone, located in association with the acceleration detector for detection of corresponding sound events, and a classification unit to classify concurrent events from the microphone and the acceleration detector, thereby to determine whether a human fall is indicated. If the event appears to be a human fall, then an alarm is raised.

21 Claims, 11 Drawing Sheets

(56) References Cited

OTHER PUBLICATIONS

Alwan et al. "A Smart and Passive Floor-Vibration Based Fall Detector for Elderly", Information and Communication Technologies, Proceedings 2nd. ICTTA '06, Damascus, Syria, IEEE, XP007908766, p. 1-5, Oct. 16, 2006.

Chan et al. "A Review of Smart Homes—Present State and Future Challenges", Computer Methods and Programs in Biomedicine, XP022688343, 91(1): 55-81, Jul. 1, 2008.

Chan et al. "Efficient Time Series Matching by Wavelets", 15th International Conference on Data Engineering, Proceedings, Signey, NSW, Australia, Mar. 23-26, 1999, XP010326220, p. 126-133, Mar. 23, 1999.

Chan et al. "Smart House Automation System for the Elderly and the Disabled", IEEE Intenational Conference on Intelligent Systems for the 21st Century, Vancouver, BC, Canada, Oct. 22-25, 1995, XP010194503, 2: 1586-1589, Oct. 22, 1995.

Demongeot et al. "Multi-Sensors Acquisition, Data Fusion, Knowledge Mining and Alarm Triggering in Health Smart Homes for Elderly People", Comptes Rendus—Biologies, XP004379742, 325(6): 673-682, Jun. 1, 2002.

Doukas et al. "Advanced Patient or Elder Fall Detection Based on Movement and Sound Data", 2nd International Conference on Pervasive Computing Technologies for Healthcare, Pervasivehealth 2008, XP031289745, p. 103-107, Jan. 30, 2008.

Doukas et al. "Human Distress Sound Analysis and Characterization Using Advanced Classification Techniques", Artificial Intelligence: Theories, Models and Applications [Lecture Notes in Computer Science], XP019107502, 5138: 73-84, Oct. 2, 2008.

Freescale "MC13192 2.4 GHz Low Power Transceiver for the IEEE® 802.15.4 Standard", Freescale Semiconductor Technical Data, Document No. MC13192, XP007908826, p. 1-24, Apr. 1, 2008.

Istrate et al. "Communication Between a Multichannel Audio Acquisition and an Information System in a Health Smart Home for Data Fusion", Internet and Multimedia Systems and Applications, IMSA 2003, XP007908809, p. 1-5, Aug. 13, 2003.

Istrate et al. "Generic Implementation of a Distress Sound Extraction System for Elder Care", Proceedings of the 28th Annual International Conference of the IEEE Engineering in Medicine and Biology Society, EMBS 2006, XP031236229, p. 3309-3312, Aug. 30, 2006.

Istrate et al. "Information Extraction From Sound for Medical Telemonitoring", IEEE Transactions on Information Technology in Biomedicine, IEEE Service Center, Los Alamitos, CA, USA, XP007908807, 10(2): 264-274, Apr. 1, 2006.

Laydrus et al. "Automated Sound Analysis System for Home Telemonitoring Using Shifted Delta Cepstral Features", 15th International Conference on Digital Signal Processing, IEEE, XP031125513, p. 135-138, Jul. 1, 2007.

Noury "A Smart Sensor for the Remote Follow Up of Activity and Fall Detection of the Elderly", Annual International IEEE-EMBS Special Topic Conference on Microtechnologies in Medicine and Biology, XP007908811, p. 314-317, May 2, 2002.

Noury et al. "Fall Detection—Principles and Methods", Proceedings of the 29th Annual International Conference of the IEEE Egineering in Medicine and Biology Society, EMBS 2007, XP031336506, p. 1663-1666, Aug. 22, 2007.

Noury et al. "Montoring Behavior in Home Using a Smart Fall Sensor and Position Sensors", 1st Annual international IEEE-EMBS Special Topic Conference on Microtechnologies in Medicine & Biology, IEEE, XP007908797, p. 607-610, Oct. 12, 2000.

Popescu et al. "A Fuzzy Logic System for Acoustic Fall Detection", Proceedings of the 2008 AAAI Symposium on Artificial Intelligence in Eldercare, XP007908814, p. 1-6, Nov. 1, 2008.

Popescu et al. "An Acoustic Fall Detector System That Uses Sound Height Information to Reduce the False Alarm Rate", 30th Annual International Conference of the IEEE Engineering in Medicine and Biology Society, EMBS 2008, Vancouver, British Columbia, Canada, Aug. 20-24, 2008, XP031347778, p. 4628-4631, Aug. 20, 2008.

Rialle et al. "Health 'Smart' Home: Information Technology for Patients at Home", Telemedicine Journal and E-Health, XP008107052, 8(4): 395-409, Dec. 1, 2002.

Robinovitch et al. "Distribution of Contact Force During Impact to the Hip", Annals of Biomedical Engineering, XP007908767, 25: 499-508, Jan. 1, 1997.

Vacher et al. "Sound Detection and Classification for Medical Telesurvey", Proceedings of the 2nd International Conference on Biomedical Engineering, Innsbruck, Austria, Feb. 16-18, 2004, XP007908810, p. 395-399, Feb. 16, 2004.

Vacher et al. "Sound Detection and Classification Through Transient Models Using Wavelet Coefficient Trees", Proceedings of the European Signal Processing Conference, XP007908813, p. 1-4, Jan. 1, 2004.

Virone et al. "A Home Health Information System Based on the Can Fieldbus", 5th IFAC Conference on Fieldbus Systems and Their Applications, Aveiro, Portugal, 708 Jul. 2003, XP007908812, p. 23-28, Jul. 7, 2003.

Virone et al. "First Steps in Data Fusion Between a Multichannel Audio Acquisition and an Information System for Home Healthcare", Proceedings of the 25th Annual International Conference of the IEEE Engineering in Medicine and Biology Society, Cancun, Mexico, Sep. 17-21, 2003, XP010693122, 2: 1364-1367, Sep. 17, 2003.

Communication Pursuant to Article 94(3) EPC Dated Feb. 16, 2011 From the European Patent Office Re. Application No. 09720116.4.

\* cited by examiner

Fig. 3: Event detection algorithm

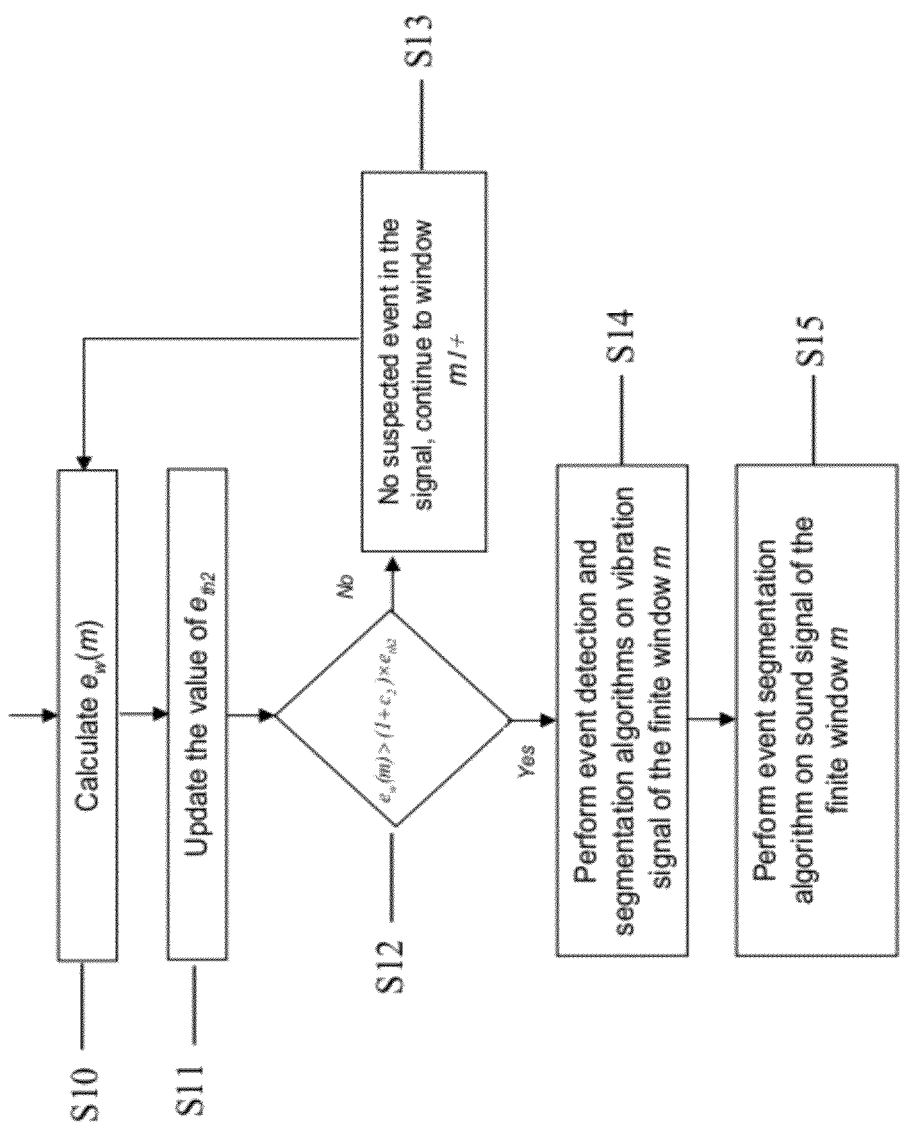
Fig. 12: Event detection and segmentation algorithms in the testing phase

SYSTEM FOR AUTOMATIC FALL DETECTION FOR ELDERLY PEOPLE

RELATED APPLICATIONS

This application is a continuation of U.S. patent application Ser. No. 12/320,521 filed on Jan. 28, 2009, which claims the benefit of priority of U.S. Provisional Patent Application No. 61/064,508 filed on Mar. 10, 2008. The contents of all of the above applications are incorporated by reference as if fully set forth herein.

FIELD AND BACKGROUND OF THE INVENTION

The present invention relates to a device and method for automatic fall detection for elderly people.

Falls are a major risk for the elderly people living independently. The statistics of falls show that approximately one in every three adults 65 years old or older falls each year, and 30% of those falls result in serious injuries. Rapid detection of fall events can reduce the rate of mortality and raise the chances to survive the event and return to independent living. In the last two decades several technological solutions for detection of falls were published, but most of them suffer from critical limitations.

The aging of baby boomers has become a social and economic challenge. Due to the maturation of the baby boomers generation, the United Nation predicts that by the year 2035, 25% of the world population will be aged 65 years or older. In the year 2000 this group accounted for 10% of population compared to 6.9% in 1900. In the United States alone, the number of people over the age 65 is expected to hit 70 million by 2030, doubling from 35 million in 2000, and similar increases are expected worldwide. This demographic trend is already posing many social and economic problems. With the aging population comes a necessity to develop more efficient and cost-effective methods of health monitoring and support for elderly people.

Falls and sustained injuries among the elderly are a major problem worldwide, and are the third cause of chronic disability according to the World Health Organization. The proportion of people sustaining at least one fall during one year varies from 28-35% for the age of 65 and over, while falls often signal the "beginning of the end" of an older person's life. The risk of falling increases with age, and in 2 cases out of 3 it happens at home. People that experience a fall event at home, and remain on the ground for an hour or more, usually die within 6 months.

In the past two decades there have been many commercial solutions and academic developments aimed at automatic and non automatic detection of falls.

A. Social alarm: The social alarm is a wrist watch with a button that is activated by the subject in case of a fall event. The main problem with that solution is that the button is often unreachable after the fall especially when the person is panicked, confused, or unconscious.

B. Automatic fall detector: The most popular solutions for automatic detection of falls are the wearable fall detectors that are based on combinations of accelerometers and tilt sensors, for example devices based on a combination of shock and tilt sensors. An alternative uses three accelerometers to obtain the position, speed and acceleration vector of the person. Noury et al. developed a device that is placed under the armpit, and employs two accelerometers and a microcontroller to compute the orientation of the body. A critical disadvantage of those solutions is that the person has to wear the device in the shower, a place with a high occurrence rate of falling, which means both that the device has to be waterproof, and furthermore people prefer not to wear anything while showering. Moreover, these devices produce many false alarms, and old people tend to forget wearing them frequently.

C. Video analysis-based fall detection system: There are a few solutions from recent years that are based on image processing of the person's movement in real-time. One work analyzes the vertical and horizontal speeds during a fall. Another develops a networked video camera system that detects moving objects, extracting features such as object speed and determines if a human fall has occurred.

Camera based solutions suffer from particular disadvantages such as privacy concerns, (critical to encouraging takeup), and difficulty in effectively monitoring the entire area of a house where falls may take place.

Due to the disadvantages of the existing fall detection techniques, there is a need for a better solution for the elderly fall detection. The idea of floor vibrations was suggested by Alwan et al. M. Alwan, P. Rajendran, S. Kell et al., "A smart and passive floor-vibration based fall detector for elderly," in *Proceedings ICTTA '06*, Damascus, Syria, April 2006, pp. 23-28.

SUMMARY OF THE INVENTION

We have developed a solution that is based on the combination of floor vibrations detection and sound during a fall, and does not require the subject to wear anything however, The present embodiments further differ over Alwan et al, in use of different sensors, features and pattern recognition algorithms that are implemented in the system. According to one aspect of the present invention there is provided apparatus for detection of human falls, comprising:

an acceleration detector, for detecting vibration events, a microphone, for placing in association with said acceleration detector for detection of sound events, and a classification unit configured to classify concurrent events from said microphone and said acceleration detector, thereby to determine whether a human fall is indicated.

There may additionally be an alarm unit, associated with said classification unit, for providing an alarm output when said human fall is indicated.

In an embodiment, said acceleration detector is attached to a floor.

In an embodiment, said concurrent events comprise vibration events, and sound events.

In an embodiment, said classification unit is configured to extract from said events a shock response spectrum (SRS) feature.

In an embodiment, said classification unit is configured to extract from said events a Mel frequency cepstral coefficient (MFCC).

In an embodiment, said classification unit is configured to extract from said sound events a sound event length feature and a sound event energy feature.

In an embodiment, said classification unit is configured to extract from said vibration events a vibration event length and a vibration event energy.

In an embodiment, said classification unit is configured to extract features from said events, and to compare a distribution of said features with prestored features of learned events, thereby to classify said events as belonging to a human fall or not belonging to a human fall.

In an embodiment, said extracted features comprise shock response spectra, Mel frequency cepstral coefficients, vibration event energy, vibration event length, sound event energy and sound event length.

In an embodiment, said extracted features comprise seventeen features.

According to a second aspect of the present invention there is provided a method for detection of human falls, comprising:

detecting vibration events,
  detecting sound events,
  classifying concurrent vibration and sound events to determine whether a human fall is indicated, and
  providing an alarm output when said human fall is indicated.

Unless otherwise defined, all technical and scientific terms used herein have the same meaning as commonly understood by one of ordinary skill in the art to which this invention belongs. The materials, methods, and examples provided herein are illustrative only and not intended to be limiting.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Implementation of the method and/or system of embodiments of the invention can involve performing or completing selected tasks manually, automatically, or a combination thereof. This refers in particular to tasks involving the control of the spectral equipment.

Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 12 is a flow chart showing event detection and segmentation algorithms used in the testing phase of the present embodiments;

DESCRIPTION OF THE PREFERRED EMBODIMENTS

Figure 1:
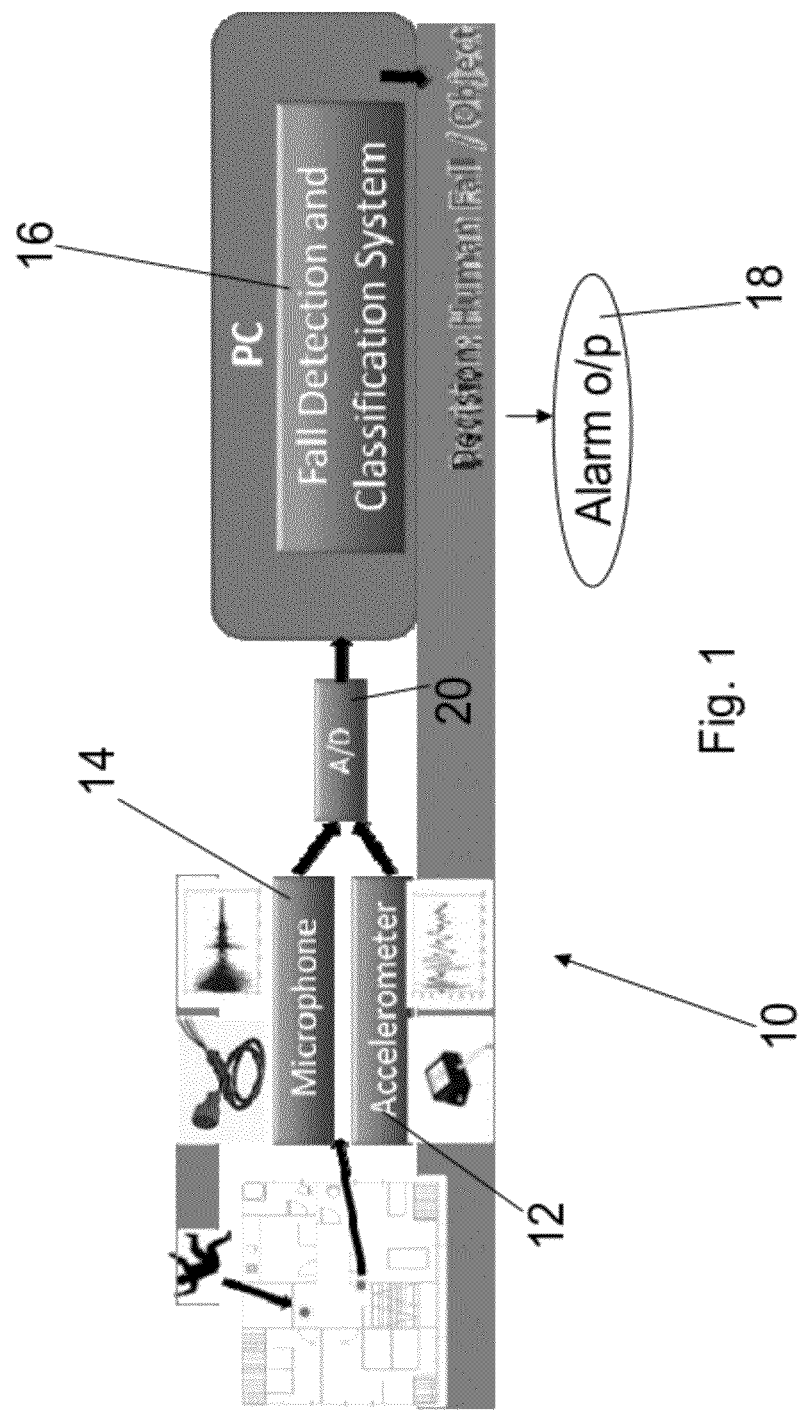
FIG. 1 is a simplified diagram illustrating a first fall detection device according to an embodiment of the present invention.

The present embodiments provide an automatic fall detection system for elderly people. The system is based on floor vibration and acoustic sensing using two or more sensors, and uses signal processing and pattern recognition algorithm to discriminate between human fall events and other events, such as inanimate object falls. The proposed solution is inexpensive, and does not require the person to wear anything. It may detect fall events in critical cases in which the person is unconscious or in a stress condition. Results obtained with an embodiment provided for detection of human falls with a sensitivity of 97.5% and specificity of 98.5%.

A human fall on the floor creates a shock signal that propagates through the floor. Any type of floor is suitable, although different floors have different properties in terms of signal transmission. In a daily routine there are a lot of sounds in the house, but, as will be described hereinafter, when there is a particular combination of a fall-specific vibration event with a corresponding sound event, there is a suspicion of a human fall on the floor. The present embodiments make use of a combination of vibration and sound sensors because they can supply information about the way the fall vibrates the floor and how it sounds. The combination is explained hereinbelow. The proposed fall detection system comprises a passive solution that does not require the person to wear anything. The system is based on the detection of vibration and sound signals from an accelerometer and a microphone. The main hypothesis is that in most cases we can accurately identify human falls and discriminate them from other events using sound and vibration detection in conjunction with advanced signal processing techniques. The present embodiments aim to provide a complete solution, which consists of an automatic algorithm that is based on signal processing and pattern recognition techniques, and is able to demonstrate detection of falls. Algorithms described herein enable a distinction to be made between a human fall event and other events such as the fall of an object on the floor, or the vibrations and sounds of mere daily activities. In the experiments herein described, an accelerometer and microphone were located at the side of a room, close to the wall, and connected to the floor by scotch tape. The accelerometer was attached to the floor, the microphone was above the accelerometer, and the scotch tape connected them both to the floor.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1 which is a generalized block diagram showing a simplified conceptual view of the fall detection system according to a first embodiment of the present invention. Apparatus 10 for detection of human falls, comprises an acceleration detector 12 for detecting vibration events. The acceleration detector is typically an accelerometer. Alternatively, any other vibration detector may be used. A microphone 14 is located in association with the acceleration detector 12 and serves for detection of sound events. Other detectors may also be used, for example humidity detectors, temperature detectors, lighting detector etc as may seem useful. The acceleration detector may be a single axis acceleration detector or multi-axis acceleration detector. A classification unit 16, typically provided within an electronic processor, classifies concurrent events detected by the microphone and the acceleration detector. The processor uses data of the event as provided by the accelerometer and the microphone, to make a decision as to whether or not a human fall is indicated. An alarm unit 18 uses the output decision of the classification unit and provides an alarm output when the human fall is indicated. The output may be provided to a relative, a care supervisor or to emergency or medical services, as deemed appropriate. In one embodiment the microphone and an associated loudspeaker may subsequently be used to open a voice channel to allow the output recipient to make voice contact in order to better assess the situation.

Typically, the acceleration detector 12 is attached to a floor, so as best to pick up vibrations caused by the fall.

The concurrent events as detected are formed by combining vibration data from the accelerometer and sound data from the microphone, into a single combined event that is assessed together.

The data received from the accelerometer and from the microphone is in the form of analogue waves. The waves may initially be digitized by A/D converter 20. Subsequently features are extracted from the waveforms and it is the extracted features which are assessed and compared. Numerous features can be derived from waveforms. As will be discussed below, a limited number of features was chosen experimentally and found in combination to define human falls with high reliability. However any other features or combination of features which is found to provide reliable identification of human falls, is contemplated by the present embodiments.

In an embodiment the classification unit is configured to extract from the events and associated waveforms a shock response spectrum (SRS) feature. Another feature is a Mel frequency cepstral coefficient (MFCC). From the sound events a sound event length feature and a sound event energy feature may be extracted. From the vibration events, a vibration event length and a vibration event energy may be extracted.

Figure 11:
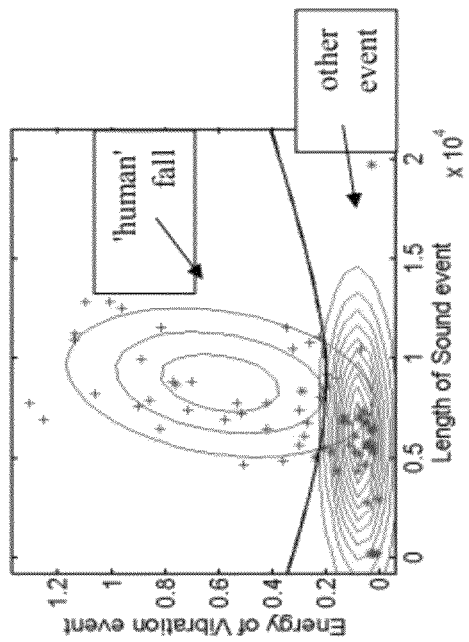
FIG. 11 is a graph of a vibration energy feature plotted against length of sound event and again showing a line that divides the graph into human fall and other event.
Figure 10:
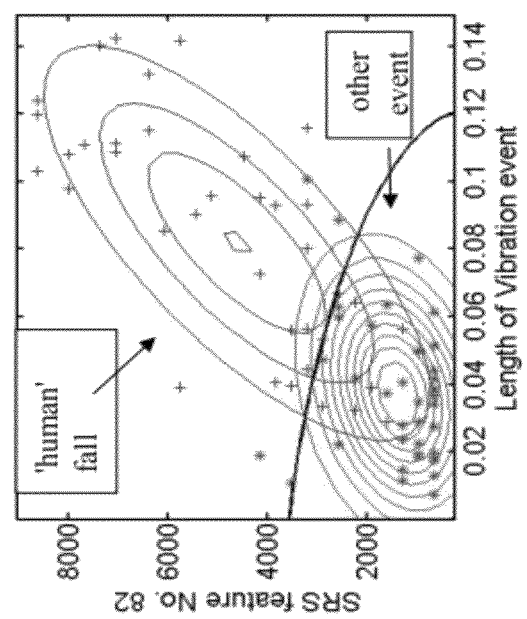
FIG. 10 is a graph of an SRS feature plotted against length of vibration event and showing a line that divides the graph into human fall and other event.

A distribution of the extracted features is then compared with distributions in prestored features of learned events. FIGS. 10 and 11, to be described below, show distributions in which a line divides human fall events from other events. The comparisons allow for classification of events as belonging to a human fall or not belonging to a human fall.

Up to seventeen different features were used in the present embodiments, although this number is merely exemplary and any other number of features may be equally as good, as will be discussed in greater detail below. Furthermore the features selected may be replaced by alternative features.

In use, the apparatus of claim 1 detects vibration events, and simultaneously detects sound events. Concurrent vibration and sound events are analyzed and features extracted. The feature distribution is compared to previously learned events to determine whether a human fall is indicated. Finally, an alarm output is provided when a human fall is indicated.

If different detectors are placed in different rooms, then an alarm may indicate which detector has been triggered, thus indicating in which room the fall occurred. Where several detectors cover a room, say in the case of a large room, the alarm may indicate in which room the fall has occurred.

In an embodiment, the sensors that are used include a Crossbow CXL02LF1Z accelerometer (San-Jose, Calif.) and a small amplified microphone (MS-3100W), both being attached to the floor. The acquired signals are transmitted to a portable NI USB-6210 (National Instruments, TX, USA) data acquisition device that samples the signals at 16 kHz and transmits them to a PC.

As a rule of thumb, if a machine produces high amplitude vibrations (greater than 10 g rms, where g is the gravitational acceleration of earth) at the measurement point, a relatively low sensitivity (10 mV/g) sensor is preferable. If the vibration is less than 10 g rms, a high sensitivity (100 mV/g) sensor should generally be used. The acceleration of the floor in an event of a human fall is in a scope of 1-2 g with low amplitude vibrations. Therefore, we choose to use an accelerometer with a sensitivity of 1 V/g with the ability to sense accelerations up to 2 g. The chosen microphone has a Frequency range of 20-16000 Hz, and S/N Ratio of more than 58 dB.

Using an energy-based event detection algorithm, floor vibrations are monitored and events are detected. Vibration and sound features are extracted from these events and classified based on a pattern recognition algorithm that discriminates human fall from other events. If the algorithm reports a human fall, an alarm is activated.

Fall Detection and Classification Algorithm

Figure 2:
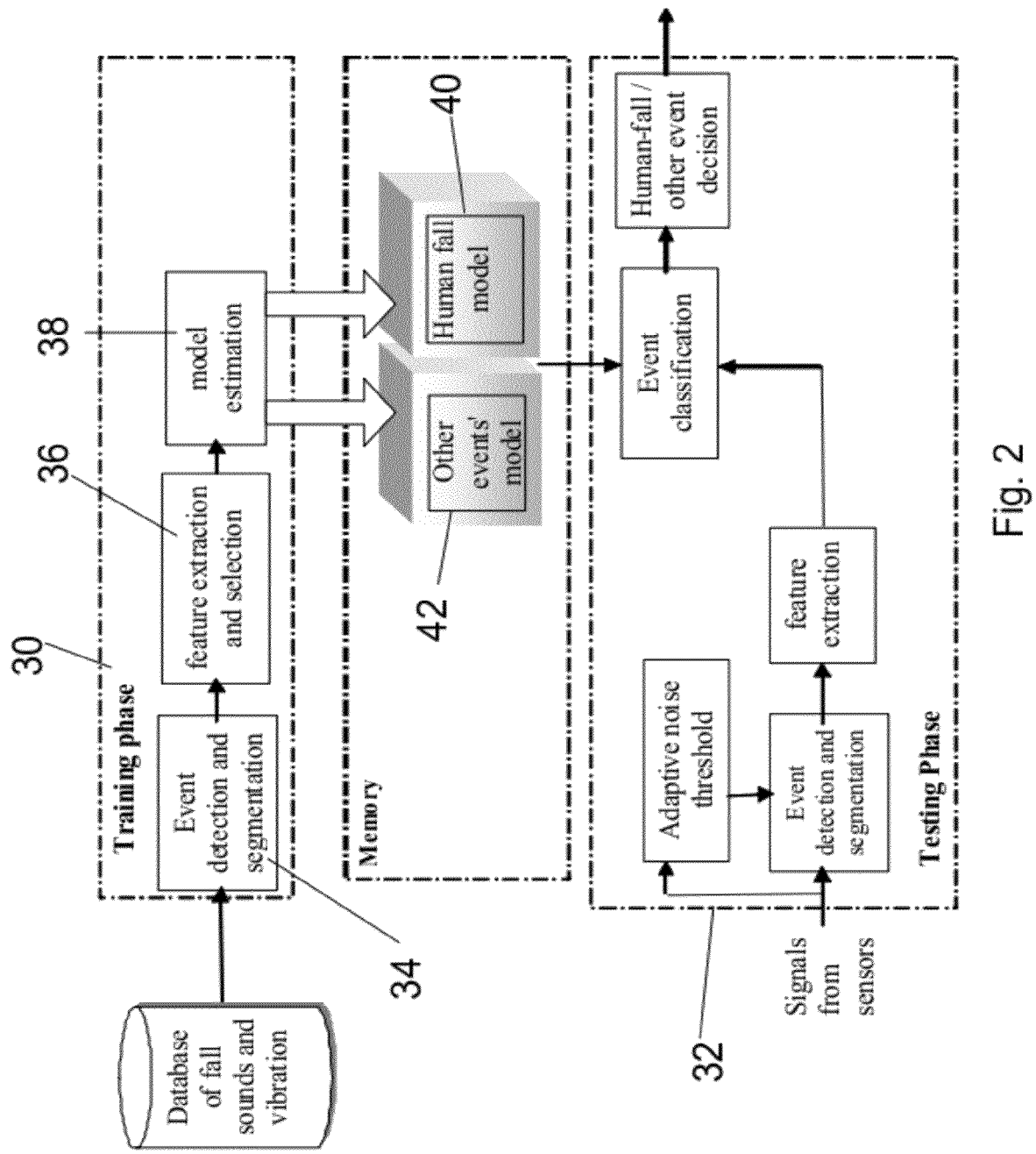
FIG. 2 is a simplified diagram showing training and testing phases in the device of FIG. 1.

A block diagram of the fall detection and classification system is shown in FIG. 2.

The system contains two phases of data analysis: a training phase 30 and a testing phase 32. Both phases use vibration and sound signals as inputs. In order to trigger the classification algorithm, a significant event in the vibration signal is found. Once an event is detected in the vibration signal, the sound signal is analyzed. The sound waves that propagate in the air are slower than the vibration waves that propagate in the floor. Nevertheless, the length of the time delay between the signals is much shorter than the time length of the events so that simultaneity can still be defined, and the analysis of the signal can be performed as will be shown ahead.

The training phase 30 consists of event detection and segmentation 34, feature extraction 36, feature selection 36 and model estimation 38 modules. In the training phase of the algorithm, we estimate two classification models for different types of events. In our system there are two classes of classification: "human fall" 40 and "other event" 42.

Event Detection and Segmentation (Training Phase)

Figure 3:
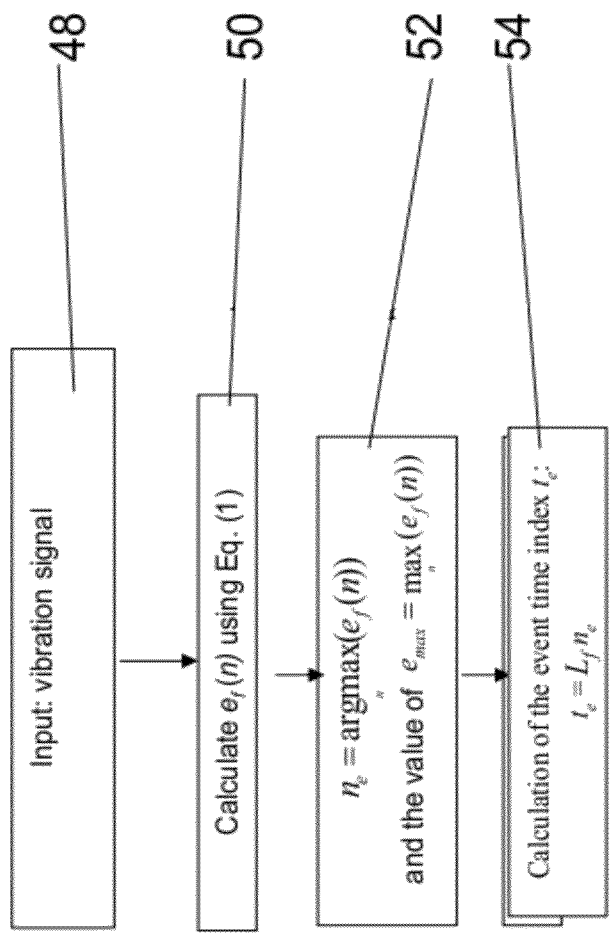
FIG. 3 shows a detail of event detection in the flow chart of FIG. 2.

Reference is now made to FIG. 3, which is a simplified flow diagram which describes detection and segmentation of a vibration event from within a vibration signal. The purpose of the event detection algorithm, module 34, is to detect a vibration event in the vibration signal v(t) at time index $t_e$, and to segment it. The event detection and segmentation are performed using energy calculations $e_f(n)$ from running timeframes:

$$e_f(n) = \sum_{t=(n-1) \times L_f}^{n \times L_f - 1} v^2(t); n = 1, \ldots, N_f - 1 \quad (1)$$

where $e_f(n)$ represents the energy of the $n^{th}$ time frame, $N_f$ is the total number of frames in the signal v(t), and $L_f$ is the length of each frame (20 msec. in this case).

Module 34 operates the event detection algorithm on a recorded finite vibration signal in the training phase. In FIG. 3, the input vibration signal is received in box 48, is entered into equation 1, in box 50, to obtain an array $e_f(n)$. Then in box 52, $e_{max}$ is obtained, being the maximum value of the array $e_f(n)$, where $n_e$ is the frame index of the event, and in box 54, $t_e$ is obtained, being the time index of the event.

Figure 4:
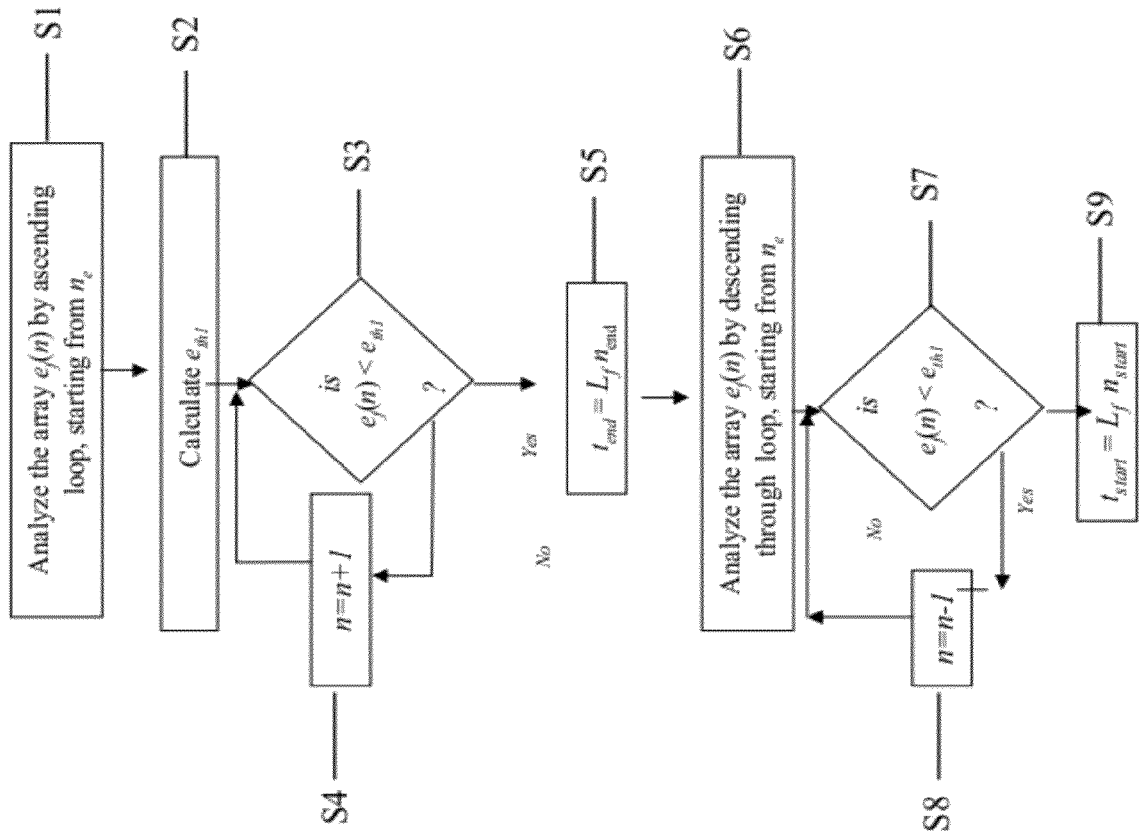
FIG. 4 shows a detail of segmentation in the flow chart of FIG. 2.

Reference is now made to FIG. 4, which illustrates the array analysis for segmentation. After finding $t_e$ by the event detection algorithm, the event segmentation algorithm extracts the event from the recorded finite vibration signal. Segmentation of the vibration event is performed by an automatic algorithm that identifies the boundaries of the event. The boundaries of the event $t_{start}$ and $t_{end}$ are calculated by an algorithm that is based on an automatic noise threshold calculation.

FIG. 4 describes the event segmentation algorithm on a recorded finite vibration signal in the training phase. In this figure $n_{end}$ represents the frame index of the end of the event, $n_{start}$ is the frame index of the beginning of the event, $t_{end}$ is the time index of the end of the event, $t_{start}$ is the time index of the beginning of the event and $e_{th1}$ is the threshold of the frame energy.

Calculation of the energy threshold $e_{th1}$: The value of $e_{th1}$ is calculated by assessing the $e_{hist}$ which is the most prominent value of $e_f(n)$. $e_{hist}$ is calculated from a binned histogram of the recorded finite vibration signal. The value of $e_{th1}$ is calculated by $$e_{th1} = e_{hist} \times (1 + c_1) \quad (2)$$

where $c_1$ is an empirical threshold coefficient (set to 0.2).

In the method the array is analyzed first by ascent to obtain the end of the event and then by descent to obtain the beginning of the loop.

Figure 5:
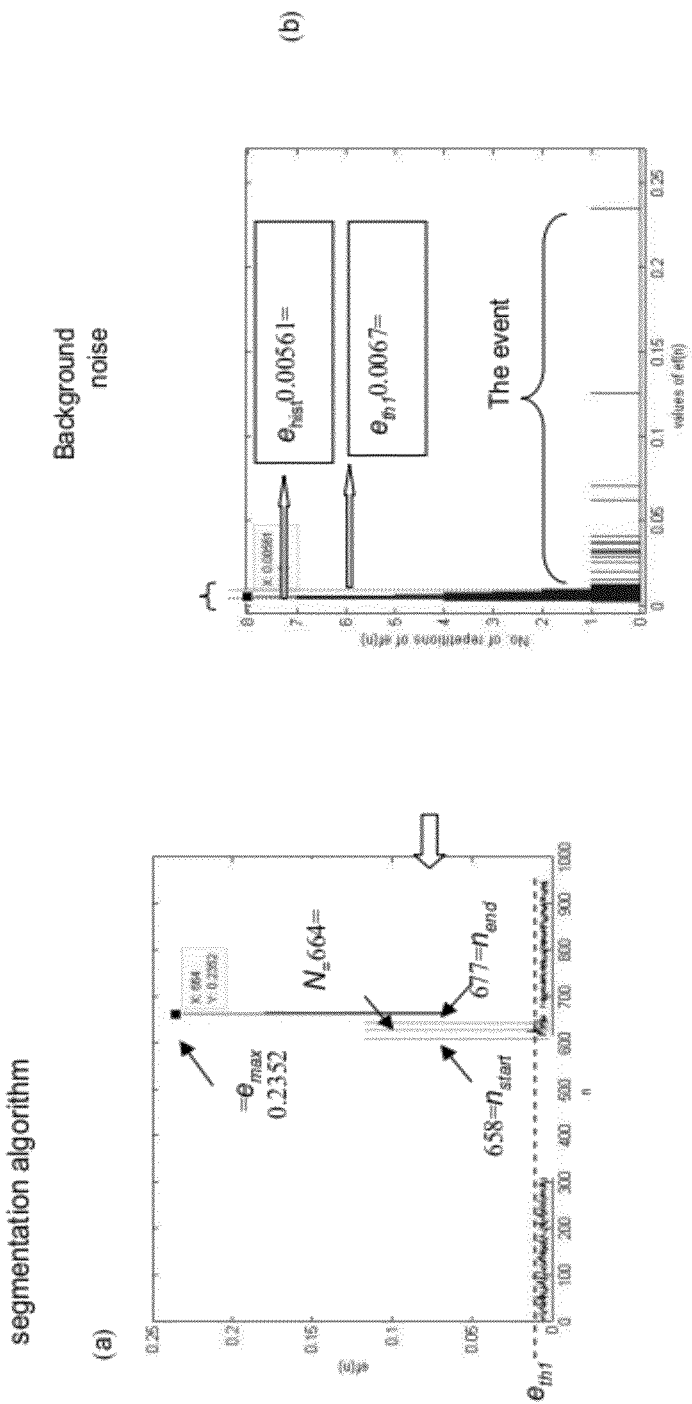
FIGS. 5a and 5b are simplified plots showing segmentation and background noise, applied to detection by the device of FIG. 1.

FIGS. 5a and 5b between them show an example of event segmentation. FIG. 5a is a figure showing three signal energies, a maximum, an event beginning and an event end. and FIG. 5b shows an example of a histogram calculation of the array $e_f(n)$ with a resolution of 0.00001. As seen in FIG. 5b, the background noise energy distribution is shown. Using the noise distribution the locations of the beginning and end of the event can be determined. The threshold in this example is calculated to be 0.0067 (using 20 msec. frame size).

After detection and segmentation of a vibration event, segmentation of the sound event from the sound signal is performed. Starting from $t_e$, the algorithm finds the boundaries of the sound event using the same segmentation technique mentioned above.

Figure 6:
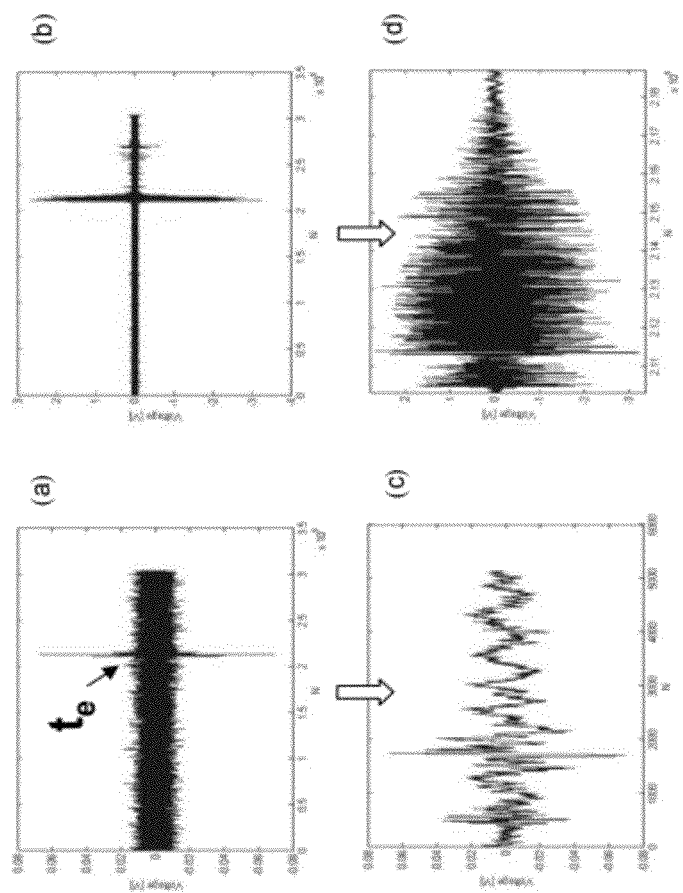
FIG. 6a shows a vibration event within a continuous signal.
FIG. 6b shows a sound event within a continuous signal.
FIG. 6c shows a vibration event after extraction.
FIG. 6d shows a sound event after extraction.

FIGS. 6a-d shows an example of the results of the event detection and segmentation algorithms implemented on a vibration and sound signals of a fall event. Specifically, FIG. 6a shows a vibration event within a continuous signal, FIG. 6b shows a sound event within a continuous signal, FIG. 6c shows a vibration event after extraction, and FIG. 6d shows a sound event after extraction. It will be appreciated that other algorithms for event segmentation are available and may be selected by the skilled person.

Feature Extraction (Training & Testing Phases)

The classification problem is to distinguish between events of human and object falls. Following the event detection and segmentation, features are extracted from these vibration and sound event signals (training phase trials) for model estimation. The selection of the complete feature set, the subset of features to be used from the complete feature set, and the design of the model which uses these selected features is of central importance for obtaining high classification accuracy. The complete set of features that were chosen as candidates for the model are composed of two kinds of features: temporal features and spectral features.

1. Temporal Features: The features that are extracted from the vibration and sound events are length (time) and energy (sum of square of the amplitudes over time), a total of four temporal features.
2. Spectral Features: Shock response spectrum (SRS) features are extracted from the vibration event signal, and Mel frequency cepstral coefficients (MFCC) may be extracted from the sound event signal.

Table 1 summarizes the overall set of the candidate features.

TABLE 1

Summary of candidate features

| Kind of feature | Feature name | No. of features | Vibration/Sound feature | Feature symbol |
|---|---|---|---|---|
| Temporal features | Vibration event length | 1 | Vibration | L1 |
| | Sound event length | 1 | Sound | L2 |

TABLE 1-continued

Summary of candidate features

| Kind of feature | Feature name | No. of features | Vibration/Sound feature | Feature symbol |
|---|---|---|---|---|
|  | Vibration event energy | 1 | Vibration | E1 |
|  | Sound event energy | 1 | Sound | E2 |
| Spectral features | SRS | 93 | Vibration | S1-S93 |
|  | MFCC | 13 | Sound | C1-C13 |

Figure 7:
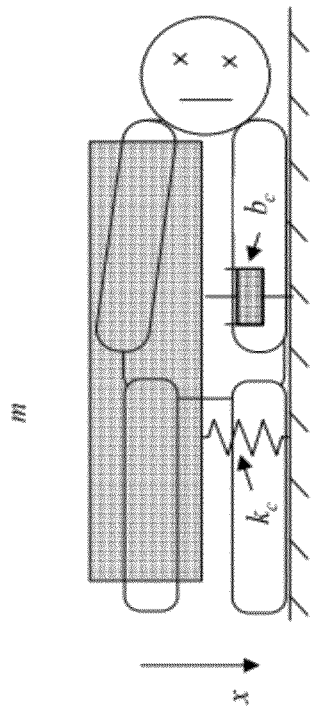
FIG. 7 is a simplified diagram showing a human as an shock response system as modeled by an embodiment of the present invention.

Shock response spectrum (SRS): For the analysis of the floor's vibration signal, we use a physical approach for the description of the human-floor system. Robinovitch et al S. N. Robinovitch, W. C. Hayes, and T. A. McMahon, "Distribution of contact force during impact to the hip," *Annals of Biomedical Engineering*, vol. 25, no. 3, pp. 499-508, 1997, describe the dynamics of impact to the hip during a fall event as a Mass-Spring system as per FIG. 7. A mass spring approach justifies the use of the shock response spectrum analysis that is popular in many engineering fields for vibration signal analysis.

Figure 8:
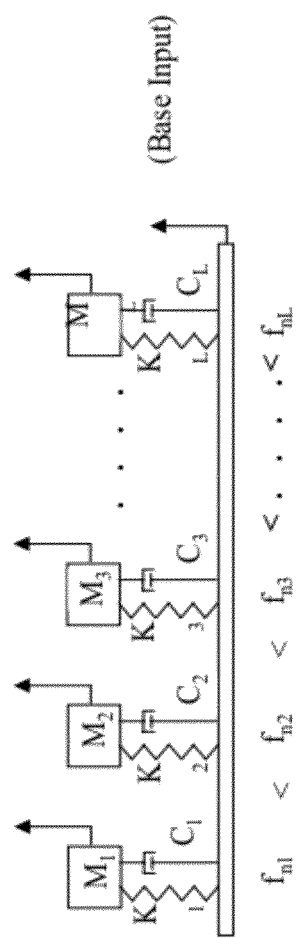
FIG. 8 is a simplified diagram showing the Shock response system model used for calculations, according to an embodiment of the present invention.

The SRS calculation is a transform that assumes that the fall event is a mass-spring system. The SRS is the peak acceleration responses of a large number of single degree of freedom (SDOF) systems each one with a different natural frequency (FIG. 8). It is calculated by convolution integral of the measured signal (input) with each one of the SDOF systems.

Figure 9:
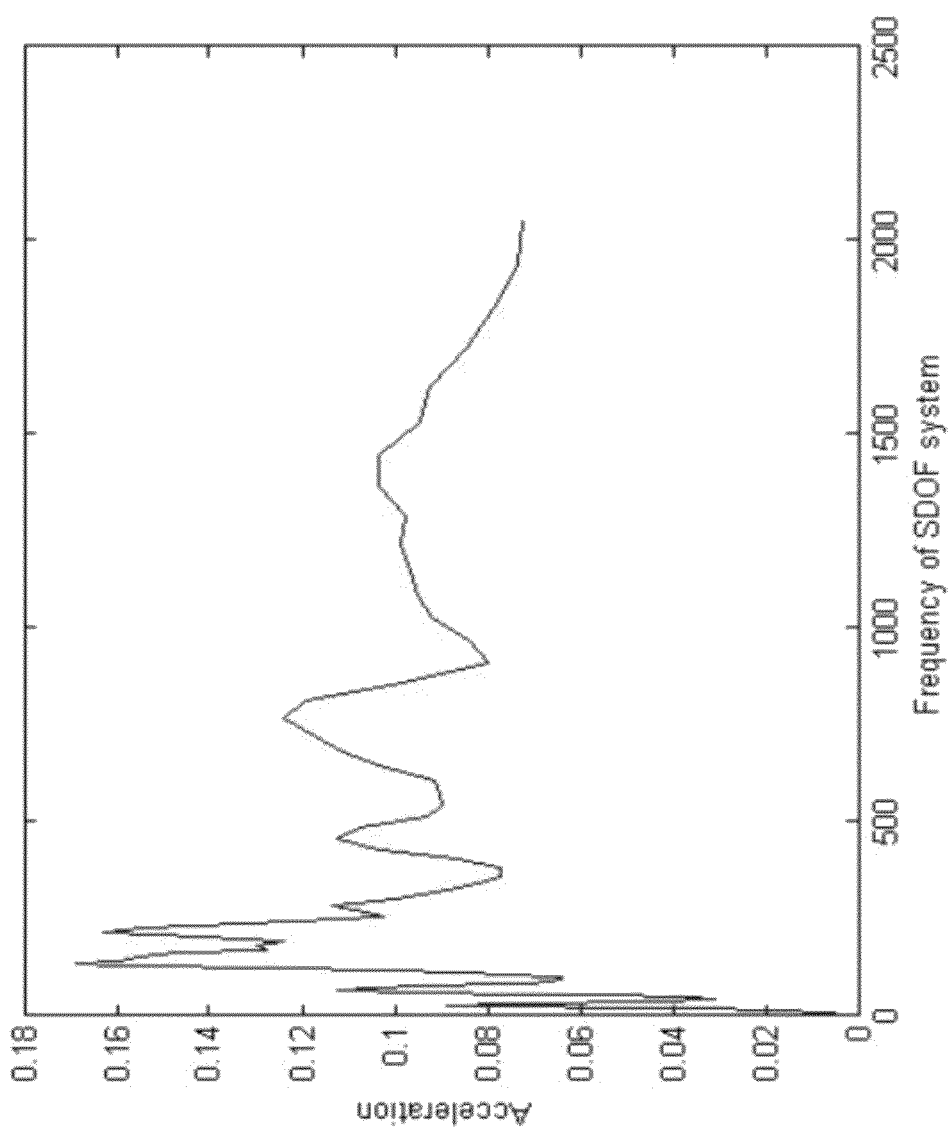
FIG. 9 is a graph showing acceleration against SDOF system frequency for a particular test event using the present embodiment.

A typical scheme of the frequencies of the x axis is based on a proportional bandwidth, such as /1;6 octave. This means that each successive natural frequency is $2^{1/6}$ times the previous natural frequency. FIG. 9 is an example of the SRS plot of one of the vibration events as measured by an accelerometer of the present embodiments. The SRS transform has a total of 133 values, but at very low frequencies many of those values are close to zero. Therefore, we choose 93 values of the SRS as candidate features from the frequency bandwidth of 10.1-2,048 Hz of a specific vibration event.

Mel frequency cepstral coefficients (MFCC): Mel Frequency Cepstral Coefficients (MFCCs) represent audio signals with frequency bands that are positioned logarithmically (on the Mel scale) and approximate the human auditory system's response more closely than the linearly-spaced frequency bands obtained directly from the FFT of the signal. The use of these coefficients is popular in speech and speaker recognition, and fits our goal of characterizing the sound of a human fall and other events. In our study there are different kinds of sound signals. The signal may vary from short events, such as human steps, to long events such as a human fall. We divide the sound event signals into windows with length of 0.03 seconds, and calculate the MFCC coefficients for each window. The MFCC transform supplies 13 features for each window, when the first feature is the energy of the window. By choosing the window with the maximum first feature, that is the most 'energetic' window, we extract 13 MFCC features from each sound event signal.

Feature Selection (Training Phase)

The problem of selecting a subset of features from N-dimensional feature measurement vector is called feature selection. The feature selection procedure reduces the cost of the pattern recognition process, and provides better classification accuracy due to finite training dataset size effects. There are several feature selection procedures discussed in the pattern recognition literature such as: sequential forward selection (SFS), sequential backward selection (SBS), l-r algorithm, sequential floating forward sequence (SFFS), and others.

The sequential forward floating selection (SFFS) method has been suggested to be the most powerful algorithm for feature selection. On this basis we use the SFFS algorithm with Mahalanobis distance test criterion for performance evaluation of the features $$D(Z) = (\mu_1 - \mu_2)^T C^{-1} (\mu_1 - \mu_2) \quad (3)$$

Where Z is the set of the feature vectors, C is the covariance matrix of the feature vector, and $\mu_1, \mu_2$ are the mean vectors of each class ("human fall" and "other event").

The Mahalanobis distance test criterion is the appropriate one for distance measurement of features with a Gaussian distribution.

Three major steps are identified in the SFFS algorithm: the first is "Inclusion", the second is "Test", and the last is "Exclusion". SFFS begins with the inclusion process to select a feature with best performance. The searching process is followed by conducting a test on every feature selected in the same iteration to specify features that may degrade the overall performance. If such a feature exists, SFFS may commence an exclusion process to ignore such a feature. The algorithm may continue looking for other better features until all features are examined.

The algorithm for feature selection ranks the performance of 110 features, as per table 1 above, and chooses a set of 17 top performing features for event classification, see the results section below.

Model and Classifier Estimation (Training Phase)

In the training phase, we use the features of "human" fall events and features of "other" events to estimate two models: a "human fall" event model and an "other" event model.

Many different algorithms have been developed to classify unknown pattern samples on the basis of a specified set of features. The classification algorithms described herein are based on Bayes classification although other algorithms are available to the skilled person.

The Bayes decision rule classifies an observation vector z to the class that has the highest a posteriori probability among the two classes $$\omega(z) = \underset{\omega \in \Omega}{\operatorname{argmax}} \{ P(\omega | z) \} \quad (4)$$

Where $\omega(z)$ is the chosen class, z is the observation feature vector, $P(\omega|z)$ is the a posteriori probability, and $\Omega = \{\omega_1, \omega_2\}$ is the class space.

The Bayes decision rule in terms of a priori probabilities and the conditional probability densities is $$\omega(z) = \underset{\omega \in \Omega}{\operatorname{argmax}} \{ p(z | \omega) P(\omega) \} \quad (5)$$

where $p(z|\omega)$ is the conditional probability density function (the likelihood function of z given $\omega$), and $P(\omega)$ is the class a priori probability.

In this study, the a priori probabilities of "human fall" events and "other" events are not known. Therefore, the a priori probabilities for the two classes are assumed to be equal. Hence, $$P(\omega_k) = \tfrac{1}{2}; \, k=1,2 \quad (6)$$

where k is the class index.

The training dataset found to have a Gaussian distribution for each class. Therefore Gaussian models were estimated for each class. The Gaussian conditional density function is $$p(z \mid \omega_k) = \frac{1}{\sqrt{(2\pi)^N |C_k|}} \exp\left(\frac{-(z-\mu_k)^T C_k^{-1}(z-\mu_k)}{2}\right) \quad (7)$$

where $C_k$ is the kth class covariance matrix, $\mu_k$ is the kth class expectation vector, and N is the feature space dimension.

The kth class expectation vector $\mu_k$ is estimated by $$\mu_k = \frac{1}{N_k} \sum_{n=1}^{N_k} z_n \quad (8)$$

where $N_k$ is the number of samples with class $\omega_k$, and $z_n$ is the measurement features vector.

The kth class covariance matrix $C_k$ is estimated by $$C_k = \frac{1}{N_k - 1} \sum_{n=1}^{N_k} (z_n - \mu_k)(z_n - \mu_k)^T \quad (9)$$

The model parameters that are stored for each class are the expectation vector $\mu_k$ and the covariance matrix $C_k$.

Substitution of (6) and (7) in (5) gives the following Bayes decision rule $$\omega(z) = \omega_i \quad (10)$$

with $$i = \underset{k=1,2}{\operatorname{argmax}} \left\{ \frac{1}{\sqrt{(2\pi)^N |C_k|}} \exp\left(\frac{-(z-\mu_k)^T C_k^{-1}(z-\mu_k)}{2}\right) \cdot \frac{1}{2} \right\}$$

We take the logarithm of the function between braces without changing the result of the argmax { } function. Therefore (10) is equivalent to $$\omega(z) = \omega_i \quad (11)$$

with $$i = \underset{k=1,2}{\operatorname{argmax}} \left\{ -\frac{1}{2} \ln |C_k| - \frac{1}{2} \cdot (z-\mu_k)^T C_k^{-1} (z-\mu_k) \right\}$$

Equation (11) calculates the maximum likelihood, and chooses class $\omega_i$ (i=1,2) for a specific vector z in the N dimensional features space. That classifier is called quadratic classifier.

Following the estimation of the models we may calculate the boundaries between the two models by using the quadratic classifier function (Eqs. (11)), and use the estimated classifier to classify events in the testing phase of the algorithm. FIGS. 10 and 11 are plots of two selected features with a quadratic classifier. Specifically FIG. 10 shows an SRS feature against length of vibration event. A curved line differentiates between human falls and other events. FIG. 11 shows vibration energy plotted against length of the corresponding sound event. Again a curved line distinguishes between the human fall and other events. The data of those Figures was collected in the training phase trials that will be discussed later.

Event Detection and Segmentation (Testing Phase)

In the testing phase the signal is continuous. Therefore, the algorithm analyzes finite windows of the vibration signal by calculating the energy of the window ($e_w(m)$), and finds a finite suspected-event window. When there is a suspected-event window, event detection and segmentation, feature extraction, and event classification algorithms are performed. Event classification is based on the estimated models of the events.

Calculation of an $m^{th}$ event-suspected window energy value $e_w(m)$ is performed by $$e_w(m) = \sum_{t=(m-1)\times Dw}^{(m-1)\times Dw + Tw} v^2(t); m = 1, 2, \ldots \quad (12)$$

where $T_w$ is the length of the event-suspected window (20 sec. in this case), $D_w$ is the time difference between event-suspected windows (10 sec. in this case), and v(t) is the vibration signal.

FIG. 12 is a simplified diagram illustrating the event detection algorithm in the testing phase. In this figure, $c_2$ is an empirical threshold coefficient (set to 0.1), and $e_{th2}$ is the time-averaged adaptive noise level.

The value of $e_{th2}$ is recalculated every $D_w$ seconds by the same technique as $e_{th1}$ is calculated, say by assessing the most prominent value of $e_w(k)$ which is calculated from a binned histogram of the preceding 10 minutes.

Event Classification (Testing Phase)

Following the segmentation of the vibration and sound event signals from the finite event-suspected window, 17 selected features are extracted from the testing data signals, in this case 13 features from vibration signals, and 4 features from sound signals.

The values of the extracted features are substituted in the 17-dimentional estimated classifier (Eqs. (11)). Following the calculation of the maximum likelihood, the classifier returns a classification result as to whether the event is a 'human fall' (Positive) or it is 'other event' (Negative).

Experimental Setup

Figure 13A:
FIGS. 13a and 13b are sequential shots in a fall test of a human mimic.
Figure 13B:

The training and testing data sets for the algorithm were taken from experiments that were performed on a typical concrete tile floor and a carpet using "Rescue Randy"—a human mimic doll of weight 74 kg. and four other common objects. Those experiments were performed at distances of 2 to 5 meter from the sensors. Moreover, we drop objects and simulate events that generate significant floor vibrations close to the sensors in order to ensure the algorithm is effective in a multitude of conditions. The drops of "Rescue Randy" are shown in FIGS. 13a-b, and were in a forward direction, based on statistics that 60% of falls that occur are in a forward direction. Typical of human falls, no two falls of "Rescue Randy" are identical.

It will be appreciated that other human mimics, or even real falls, may be used to provide training data for the system.

Training Phase Trials

In the training phase, "Rescue Randy" was dropped 10 times at each distance, for a total of 40 drop events. The objects that were dropped on the floor include a heavy bag (15 kg.), a book, a plastic box and a metal box. The objects were dropped 5 times at each distance, a total of 20 times for each object, and thus a total of 80 drops of objects. With increase in distance from the sensors some of the non-human drops were not detected at all, and in fact only 28 of the 80 drops of the objects were detected as falling events. Therefore, only 28 events of falling objects in distances of 2-5 meters were included in the training set of data. The other trials that were performed close to the sensors included: walking, dropping a chair, jumping from the chair on the floor, dropping a heavy bag, dropping a plastic box, and dropping a metal box for a total of 12 events. Furthermore each trial was repeated twice. In total, the training set of data included 40 human falls and 40 drops of objects and other events (28+12).

Testing Phase Trials

A second, testing, phase was carried out to see how well the training phase had worked. In the testing phase, trials consisted of 20 drops of "Rescue Randy" made up of 5 repetitions in each distance of 2-5 meters, and 48 drops of objects made up of 4 kinds of objects, each one with 3 repetitions at each distance. Additional trials were performed close to the sensors, in the same way as in the training phase, and these included 3 repetitions of each event for a total of 18 events.

Furthermore, due to the fact that some apartments may be carpeted, we also performed a testing set of experiments on a carpet. There were 5 drops of "Rescue Randy" at distances of 2 to 5 meters on a carpet for a total of 20 events. The testing set of data included a total of 40 drops of "Rescue Randy" and 66 drops of objects and other events. In practice a system may be calibrated in situ based on the local floor type or floor covering. An alternative is to provide a system with calibrations for all kinds of floors. The signals may be transformed based on the local type of floor to a uniform or normalized signal so that signals from different kinds of floors can be classified by the same kind of classifier.

Results

A. Feature Selection:

The algorithm for feature selection ranked the performance of 110 features that may be extracted from the training data. A set of 17 top performing features was extracted for classification. Those features are: Lengths of vibration and sound event signals, Energy of vibration event signal, 11 SRS features and 3 MFCC features. Table 2 summarizes the overall set of the selected features for classification.

TABLE 2

Features for classification

| Feature name | Feature symbol | Selected features |
|---|---|---|
| Vibration event length | L1 | L1 |
| Sound event length | L2 | L2 |
| Vibration event energy | E1 | E1 |
| Sound event energy | E2 | — |
| SRS | S1-S93 | S2, S10, S34, S64, S68, S74, S76, S77, S82, S84, S91 |
| MFCC | C1-C13 | C3, C11, C12 |

Figure 14:
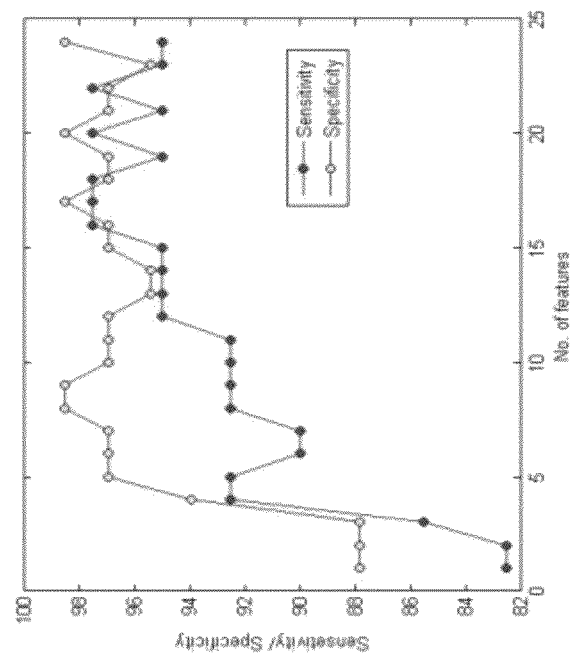
FIG. 14 is a graph of percentage success rate for sensitivity and specificity as shown by the results of the presently described tests.

During the process of the decision on the number of features for classification, an aim was to obtain sensitivity and specificity of the classification algorithm that are higher than 97%. Reference is now made to FIG. 14 which plots sensitivity against number of features. As shown in FIG. 14, the required sensitivity and the specificity are achieved when the classification is performed by 17 features. Increasing the number of features for classification beyond 17, does not increase the performance of the classification algorithm, and can cause over-fitting. Therefore, that number may be the optimal number of features for classification.

B. Testing Phase Event Classification:

Table 3 summarizes the results of the detection and classification algorithm that was run on the testing database of the trials. Cases in which no event is detected may be classified as another event.

TABLE 3

Classification Results

| | Real | | | |
|---|---|---|---|---|
| Class. As | Objects ("other event") | Events close to the sensors ("other event") | "human" | "human" on a carpet |
| "other event" | 44 (+4 undetected) | 17 | 1 | 0 |
| "human" | 0 | 1 | 19 | 20 |

A Positive event is classified as a "human fall" event, and a negative event is classified as an "other event". From the data presented, we find the sensitivity of the system to be 97.5% and the specificity to be 98.5%. The sensitivity of the system was calculated as the number of "Rescue Randy" drops that classified "human" (true positive) divided to the total number of "Rescue Randy" drops (39/40). The specificity of the system was calculated as the number of objects and events close to the sensor that may be classified as "other event" (true negative) divided by the total number of object drops and events close to the sensor (65/66). It should be mentioned that in the case of a false negative, "Rescue Randy" fell at a distance of 5 meter from the sensors. In the cases of false positive, the object fell close to the sensors generating strong signals that are similar to a human fall, and therefore classified as "human".

General

The results of the laboratory tests of the present embodiment for fall detection show that the system may serve as a solution to the discussed problem. Assuming that "Rescue Randy" is a good model for simulation of human being fall events, the system can detect human falls with high precision for distances up to 5 meters. The proposed solution is a low cost solution, does not require the person to wear anything, and is considerate of privacy. The system is adaptive, can be calibrated to any kind of floor and room acoustics, and can be used not only in personal homes but also in nursing homes.

In all the trials of "Rescue Randy" on the carpet, the events were classified as "human". The conclusion of that result is that the classification algorithm is strong enough for cases of human fall detection in which the classifier was not trained before. In cases of object drops in distances of 2 to 5 meter, in the training process 28 out of 80 event were detected, and in the testing phase 44 out of 48 event were detected. In total, 56.25% (=28+44/80+48) of the object drops were detected. The system is thus demonstrated to be successful at detection of human falls and effective at not falsely detecting other events. The difference between the percentage of detected object drops in the training phase and the testing phases can be explained by higher SNR in the testing phase signals. Object drop events create low amplitude vibration signals that sometimes cannot be distinguished from the surrounding noise. The change in the SNR can be explained by variations in the system voltage on the days that the training and testing phase experiments were performed. In cases of "Rescue Randy" drops in the training and testing phases, all the events were detected, and sent for classification. A conclusion is that the present system is sensitive enough for the detection of human fall events. High sensitivity of the event detection algorithm proves that the chosen accelerometer was a good choice for measurement of floor vibration signals. Moreover, the classification algorithm may detect falls of objects at distances of 2 to 5 meter with a precision of substantially 100%. This means that if the sensors of the proposed system are put in places in which there is a low chance of objects falling close to the sensors, the only positive events will be human falls. It is important to note that the empirical threshold coefficient $c_2$ that was set to 0.1 was good enough for the detection of all event-suspected windows in the testing phase.

One limitation of the system is that it may not be sensitive to low impact real human falls in some cases that were not tested, e.g. slow and soft human falls onto the floor from a chair. However, the kind of falls that are capable of structural damage to bone, and in which the person cannot get up, cause high amplitude floor vibrations that can be detected by the system.

In deployment, the classification algorithm may be improved by training of the classification model, using various weights of "Rescue Randy" dolls in a wider variety of kinds of drops. Moreover, the algorithm may be trained with drops of more objects on the floor and carpet, and with other events such as walking, door slams, environmental noise, and etc. that result in significant floor vibration and have sufficient energy to trigger the event detection algorithm. Tests that may further improve the performance of the system include drops of "Rescue Randy" and the objects at distances that are larger than 5 meters. Evaluation of the distance in which the sensitivity is lower than 95% may help in planning the location and number of the sensors, particularly in big rooms. Generally a deployment may require one accelerometer and microphone in a small room (~10 m2), and two such sensor units in a large room (~25 m2). The sensors may be installed in one of the corners of the room.

For now, the event detection algorithm that is based on energy calculations is relatively simple. Specific in-situ testing may also be advisable to ensure detection of 'soft' human falls and events in which the individual collides with another object, say a table, dresser, chair etc.

Ambient noise such as music and TV was found not to influence the detection because the algorithm has to detect a vibration event to correspond to the sound. In spite of that, ambient noise could conceivably influence the classification of the vibration event if say a television thump or scream happens to coincide with an actual but non-fall related vibration event.

Training in the above tests was carried out on a typical concrete floor. Concrete transfers vibration signals with high attenuation because it has sand under the tiles that absorbs the energy of the events. We preferred to choose that kind of floor because we wanted the algorithm to be able to detect and classify the events in real conditions. In real life settings a large range of different constructions, floor cover materials, and etc. exist. This may potentially have a significant effect on the signals. Therefore, in the process of actual deployment there may be a process of calibration of the algorithms to the kind of floor.

As additional features, the fall detection system may be activated by detection of a human call for help, thus by the detection of a person's scream or crying, for example using a speech detection algorithm.

The contact with the emergency center in case of a detected fall event may be performed through the sensor units. In such a case these would include not only a microphone, but also a speaker.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Apparatus for detection of human falls, comprising:
    an acceleration detector, for detecting vibration events,
    a microphone, for placing in association with said acceleration detector for detection of sound events, and
    a classification unit comprising an acceleration input for input of data relating to said vibration events from said acceleration detector and a sound input for input of data relating to said sound events from said microphone, the unit configured to classify separate events from said microphone and said acceleration detector respectively as being concurrent events, and to determine from said concurrent events whether a human fall is indicated wherein said acceleration detector is attached to a floor, said classification unit is configured to extract features from said events, and to compare a distribution of said features with prestored features, thereby to classify said events as belonging to a human fall or not belonging to a human fall, and wherein said extracted features comprise sound event energy and sound event length and four members of the group consisting of shock response spectra, Mel frequency cepstral coefficients, vibration event energy and vibration event length.

2. The apparatus of claim 1, further comprising an alarm unit, associated with said classification unit for providing an alarm output when said human fall is indicated.

3. The apparatus of claim 1, wherein said concurrent events comprise vibration events, and sound events.

4. The apparatus of claim 3, wherein said classification unit is configured to extract from vibration data of said concurrent events a shock response spectrum (SRS) feature.

5. The apparatus of claim 3, wherein said classification unit is configured to extract from sound data of said concurrent events a Mel frequency cepstral coefficient (MFCC).

6. The apparatus of claim 3, wherein said classification unit is configured to extract from said sound events a sound event length feature and a sound event energy feature.

7. The apparatus of claim 3, wherein said classification unit is configured to extract from said vibration events a vibration event length and a vibration event energy.

8. The apparatus of claim 1, further comprising an event segmentation unit, associated with said acceleration detector, operative to segment detected vibrations into events.

9. The apparatus of claim 8, wherein said event segmentation comprises using energy calculations over running time frames to identify respective events as at least one high energy time frame bounded before and after by respective low energy time frames.

10. Method for detection of human falls implemented on an electronic processor, the method comprising:
 electronically detecting vibration events,
 electronically detecting sound events, and
 defining concurrent events by combining concurrent vibration events, and sound events;
 classifying vibration and sound events detected at the same time as concurrent vibration and sound events, and
 determining from said concurrent events whether a human fall is indicated; wherein said classifying comprises extracting features from said events, and comparing a distribution of said features with prestored features, thereby to classify said events as belonging to a human fall or not belonging to a human fall; and
 wherein said extracted features comprise sound event energy and sound event length and at least four members of the group consisting of shock response spectra, Mel frequency cepstral coefficients, vibration event energy, and vibration event length.

11. The method of claim 10, further comprising providing an alarm output when said human fall is indicated.

12. The method of claim 10, comprising attaching an acceleration detector to a floor, therefrom to obtain sound events.

13. The method of claim 10, wherein said classifying comprises extracting from vibration data of said concurrent events a shock response spectrum (SRS) feature.

14. The method of claim 10, wherein said classifying comprises extracting from sound data of said concurrent events a Mel frequency cepstral coefficient (MFCC).

15. The method of claim 10, wherein said classifying comprises extracting from said sound events a sound event length feature and a sound event energy feature.

16. The method of claim 10, wherein said classifying comprises extracting from said vibration events a vibration event length and a vibration event energy.

17. The method of claim 10, further comprising event segmentation, said event segmentation comprising segmenting said detected vibrations into vibration events, and segmenting said detected sounds into sound events.

18. The method of claim 17, wherein said event segmentation comprises using energy calculations over running time frames to identify respective events as at least one high energy time frames bounded before and after by respective low energy time frames.

19. Apparatus for detection of human falls, comprising:
 an acceleration detector, for detecting vibration events,
 a microphone, for placing in association with said acceleration detector for detection of sound events, and
 a classification unit comprising an acceleration input for input of data relating to said vibration events from said acceleration detector and a sound input for input of data relating to said sound events from said microphone, the unit configured to classify separate events from said microphone and said acceleration detector respectively as being concurrent events, and to determine from said concurrent events whether a human fall is indicated wherein said acceleration detector is attached to a floor, said classification unit is configured to extract features from said events, and to compare a distribution of said features with prestored features of learned events, thereby to classify said events as belonging to a human fall or not belonging to a human fall, and wherein said extracted features comprise sound event energy and sound event length and one member of the group consisting of shock response spectra, Mel frequency cepstral coefficients, vibration event energy and vibration event length, wherein said classification unit is configured to extract said features by grouping said features over a series of tests into included and excluded features based on the feature's ability to discriminate a respective event.

20. The apparatus of claim 19, wherein said extracting is by a process of sequential forward floating selection.

21. Apparatus for detection of human falls, comprising:
 an acceleration detector, for detecting vibration events,
 a microphone, for placing in association with said acceleration detector for detection of sound events, and
 a classification unit configured to classify concurrent events from said microphone and said acceleration detector, thereby to determine whether a human fall is indicated, wherein said classification unit is configured to extract features from said events, and to compare a distribution of said features with prestored features of learned events, thereby to classify said events as belonging to a human fall or not belonging to a human fall, and said extracted features comprise sound event energy and sound event length and at least one member of the group consisting of shock response spectra, Mel frequency cepstral coefficients, vibration event energy and vibration event length, wherein said classification unit is configured to extract said features by grouping said features over a series of tests into included and excluded features based on the feature's ability to discriminate a respective event.

* * * * *